United States Patent [19]

Bastian et al.

[11] 4,031,225

[45] June 21, 1977

[54] 4H-BENZO[4,5]CYCLOHEPTA[1,2-b]THIO-PHENES

[75] Inventors: Jean-Michel Bastian, Therwil; Richard Berthold, Bottmingen, both of Switzerland

[73] Assignee: Sandoz Ltd., Basel, Switzerland

[22] Filed: June 14, 1976

[21] Appl. No.: 695,384

[30] Foreign Application Priority Data

June 18, 1975 Switzerland .................. 7922/75

[52] U.S. Cl. .................. 424/267; 260/293.57; 260/326.5 SA; 260/332.3 P; 424/274; 424/275

[51] Int. Cl.² .................. C07D 409/12

[58] Field of Search ............ 260/293.57, 326.5 SA, 260/332.3 P; 424/267, 274, 275

[56] References Cited

UNITED STATES PATENTS 3,856,818  12/1974  Hauck et al. .................. 260/340.5

Primary Examiner—G. Thomas Todd
Attorney, Agent, or Firm—Gerald D. Sharkin; Robert S. Honor

[57] ABSTRACT

This invention provides new compounds of formula I,

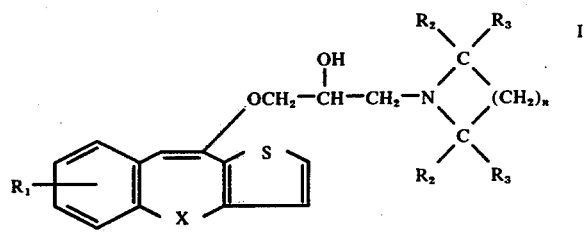

wherein
  $n$ is a whole number from 1 to 3,
  $R_1$ is hydrogen, or halogen of atomic number from 9 to 35,
  each of the two radicals $R_2$ are the same, and each is hydrogen or alkyl of 1 to 4 carbon atoms,
  each of the two radicals $R_3$ are the same, and each is hydrogen or alkyl of 1 to 4 carbon atoms, and
  X is carbonyl or methylene,
useful as anti-arrhythmics.

9 Claims, No Drawings

4H-BENZO[4,5]CYCLOHEPTA[1,2-b]THIOPHENES

The present invention relates to benzocycloheptathiophene derivatives.

The present invention provides compounds of formula I,

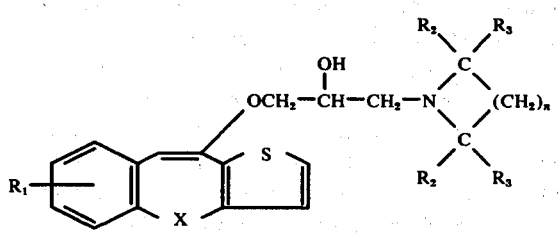

wherein
- $n$ is a whole number from 1 to 3,
- $R_1$ is hydrogen, or halogen of atomic number from 9 to 35,
- each of the two radicals $R_2$ are the same, and each is hydrogen or alkyl of 1 to 4 carbon atoms,
- each of the two radicals $R_3$ are the same, and each is hydrogen or alkyl of 1 to 4 carbon atoms, and
- X is carbonyl or methylene.

$n$ is preferably 2 or 3. Halogen is preferably chlorine or bromine, especially chlorine. Alkyl contains preferably 1 or 2 carbon atoms, especially 1 carbon atom. $R_1$ is preferably hydrogen. When $R_1$ is halogen, this is preferably in the 6 or 7 position of the tricyclic moiety. The four radicals $R_2$ and $R_3$ are preferably identical and are preferably alkyl. If $R_2$ is not the same as $R_3$, $R_3$ is preferably hydrogen.

X is preferably carbonyl.

The present invention provides a process for the production of a compound of formula I, as defined above, which comprises reacting a compound of formula II,

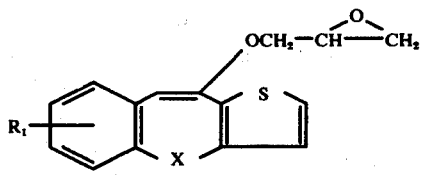

wherein X and $R_1$ are as defined above, or a reactive functional derivative thereof, with a compound of formula III,

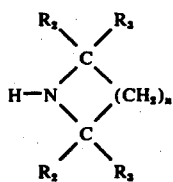

wherein $R_2$, $R_3$ and $n$ are as defined above.

The reaction may be effected in conventional manner for the production of analogous 3-amino-2-hydroxypropoxy derivatives. Suitable reactive functional derivatives of a compound of formula II include the addition product of a compound of formula II with a compound of formula

HY wherein Y is halogen or a group $R_4—SO_2—O—$ wherein $R_4$ is phenyl, tolyl, or lower alkyl. Preferably Y is chlorine or bromine. Conveniently the amine of formula III is present in an excess over the compound of formula II. Optionally there is used an inert organic solvent.

When $R_2$ is not the same as $R_3$, a compound of formula I may exist as the cis or trans isomer, which may be produced for example by using the corresponding cis or trans isomer of a compound of formula III, respectively.

The compounds of formula II are new. They may be produced in conventional manner from the corresponding 10-methoxy-4H-benzo[4,5]cyclohepta[1,2-b]thiophen-4-one, for example as described in the Examples.

Insofar as the production of any starting material is not particularly described these compounds are known, or may be produced and purified in accordance with known processes, or in a manner analogous to processes described herein, e.g. in the Examples, or to known processes.

Free base forms of compounds of formula I may be converted into acid addition salt forms in conventional manner and vice versa. Suitable acids for salt formation include hydrochloric acid.

In the following Examples all temperatures are in degrees Centigrade and are uncorrected.

EXAMPLE 1

10-[2-Hydroxy-3-(2,2,5,5-tetramethyl-1-pyrrolidinyl)-propoxy]-4H-benzo[4,5]cyclohepta[1,2-b]thiophen-4-one 20.0 g of a mixture of 10-(2,3-epoxypropoxy)-4H-benzo[4,5]cyclohepta[1,2-b]thiophen-4-one and 10-(3-chloro-2-hydroxypropoxy)-4H-benzo[4,5]cyclohepta[1,2-b]thiophen-4-one are boiled at reflux in 65 ml of 2,2,5,5-tetramethylpyrrolidine and 200 ml of methanol for 5 hours. The reaction mixture is evaporated to dryness and the residue is taken up in 600 ml of chloroform and 150 ml of 3N caustic soda solution. The organic solution is separated and is washed thrice with 3N caustic soda solution. After washing neutral with water, the solution is dried over sodium sulphate and concentrated by evaporation. The residue is chromatographed on 600 g of silica gel with a mixture of chloroform containing 5% methanol to give the title compound in free base form. (M.Pt. 104° – 107° from isopropanol).

The mixture of 10-(2,3-epoxypropoxy)-4H-benzo[4,5]cyclohepta[1,2-b]thiophen-4-one and 10-(3-chloro-2-hydroxypropoxy)-4H-benzo[4,5]cyclohepta[1,2-b]thiophen-4-one used as starting material may be produced as follows:

a. 20.0 g of 10-methoxy-4H-benzo[4,5]cyclohepta[1,2-b]-thiophen-4-one are heated to the boil at reflux with 200 ml of 6N hydrochloric acid for 2.5 hours, and then cooled to 20°. The precipitated product is filtered off. The 10-hydroxy-4H-benzo[4,5]cyclohepta[1,2-b]-thiophen-4-one has a M.Pt. of 213° (from ethanol).

b. A mixture of 15.0 g of 10-hydroxy-4H-benzo[4,5-]cyclohepta[1,2-b]thiophen-4-one, 150 ml of epichlorohydrin and 0.7 ml of piperidine is heated to the boil for 30 minutes. After concentration by evaporation at reduced pressure, the mixture is dried at 40°, whereupon a mixture of 10-(2,3-epoxypropoxy)-4H-benzo[4,5]-cyclohepta[1,2-b]thiophen-4-one and 10-(3-chloro-2-hydroxypropoxy)-4H-benzo[4,5]cyclohepta[1,2-b]thiophen-4-one is obtained, which is used further as such.

In analogous manner to that described in Example 1, the following compounds of formula I are produced from the corresponding epoxide of formula II and/or the corresponding 3-chloro-2-propanol derivative of the compound of formula II with the appropriate compound of formula III, wherein

| Ex. No. | X | $R_1$ | $R_2$ | $R_3$ | n | M.Pt. |
|---|---|---|---|---|---|---|
| 2[a)] | $CH_2$ | H | $CH_3$ | $CH_3$ | 2 | 146°–148° (decomp.) |
| 3 | CO | H | $CH_3$ | $CH_3$ | 3 | 140°–142° |
| 4 | CO | 7-Cl | $CH_3$ | $CH_3$ | 2 | 163°–165° |
| 5 | CO | 7-Cl | $CH_3$[b)] | H | 3 | 178°–180° |

[a)]The 10-methoxy-4H-benzo[4,5]cyclohepta[1,2-b]thiophene (M.Pt.) 94°–96°) required as an intermediate is produced by reacting under anhydrous conditions 10-methoxy-4H-benzo[4,5]cyclohepta[1,2-b]thiophen-4-one with lithium aluminium hydride in ether in the presence of aluminium chloride, the reaction mixture being finally stirred for 1.5 hours at room temperature.
[b)]Both groups $R_2$ are cis to each other. The compound of formula III used is cis-2,6-dimethylpiperidine.

a. The 10-methoxy-4H-benzo[4,5]cyclohepta[1,2-b]thiophene (M.Pt. 94°–96°) required as an intermediate is produced by reacting under anhydrous conditions 10-methoxy-4H-benzo[4,5]cyclohepta[1,2-b]thiophen-4-one with lithium aluminium hydride in ether in the presence of aluminium chloride, the reaction mixture being finally stirred for 1.5 hours at room temperature.

b. Both groups $R_2$ are cis to each other. The compound of formula III used is cis-2,6-dimethylpiperidine.

In analogous manner to that exemplified in Example 1 there may be produced compounds of formula I, wherein $R_1$ is 6-Br, X is $CH_2$, n is 1 and
 i. $R_2 = R_3 = H$, and
 ii. $R_2 = H$, $R_3 = $ n-propyl, and the $R_3$ groups are trans to each other.

The compounds of formula I are useful because they possess pharmacological activity in animals. In particular they are useful as anti-arrhythmic agents, e.g. for the treatment of heart rhythm disorders such as heart flutter as indicated in standard tests, for example by a protection against cardiac arrhythmia induced by chloroform in mice on i.p. administration of from 3 to 50 mg/kg animal body weight of the compounds in accordance with the principles of J. W. Lawson [J. Pharmacol. Exp. Therap. (1968) 160 22–31].

For this use the dosage will, of course, vary depending on the compound employed, mode of administration and treatment desired. However, in general, satisfactory results are obtained with a daily dosage of from about 0.1 mg to about 50 mg/kg animal body weight, conveniently given in divided doses 2 to 4 times a day or in sustained release form. For the larger mammal, the total daily dosage is in the range from about 10 to about 100 mg, and dosage forms suitable for oral administration comprise from about 2 mg to about 50 mg of the compounds admixed with a solid or liquid pharmaceutical carrier or diluent.

A preferred group of compounds comprises those wherein X is carbonyl, $R_1$ is hydrogen, chlorine or bromine, in the 6 or 7 position, $R_2$ and $R_3$ are alkyl of 1 or 2 carbon atoms and n is 2 or 3.

The Example 1 compound shows particularly interesting properties.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent. Such compositions may be in the form of, for example, a solution or a tablet.

The compounds of formula I may be administered in pharmaceutically acceptable acid addition salt form. Such acid addition salt forms exhibit the same order of activity as the free base forms and are readily prepared in conventional manner. Representative acid addition salt forms include organic acid salt forms such as the hydrogen maleate, fumarate, tartrate and methane sulphonate and mineral acid salt forms such as the hydrochloride, hydrobromide and sulphate. A pharmaceutical composition may comprise a compound of formula I, in free base form or in pharmaceutically acceptable acid addition salt form, in association with a pharmaceutical carrier or diluent. Such compositions conveniently contain more than 1% by weight of the compound of formula I and may be prepared by conventional techniques to be in conventional forms, for example, capsules, tablets, suppositories, dispersible powders, syrups, elixirs, suspensions or solutions, for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia, and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period.

The preferred compositions from the standpoint of ease of administration are solid compositions, particularly solid-filled gelatin capsules and tablets.

We claim:
1. A compound of formula I,

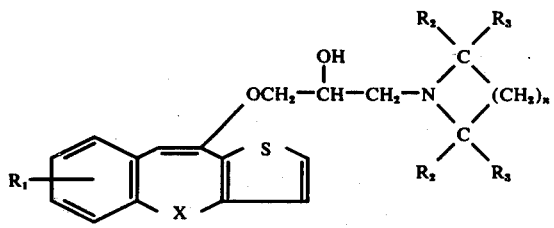

wherein
  $n$ is a whole number from 1 to 3,
  $R_1$ is hydrogen, or halogen of atomic number from 9 to 35,
  each of the two radicals $R_2$ are the same, and each is hydrogen or alkyl of 1 or 4 carbon atoms,
  each of the two radicals $R_3$ are the same, and each is hydrogen or alkyl of 1 to 4 carbon atoms, and
  X is carbonyl or methylene,
in the form of the free base or in the form of a pharmaceutically acceptable acid addition salt thereof.

2. The compound of claim 1 which is 10-[2-hydroxy-3-(2,2,5,5-tetramethyl-1-pyrrolidinyl)-propoxy]-4H-benzo[4,5]cyclohepta[1,2-b]thiophen-4-one.

3. A pharmaceutical composition comprising a compound of claim 1 in association with a pharmaceutical carrier or diluent.

4. A method of treating animals with heart rhythm disorders, which comprises administering to an animal in need of such treatment a therapeutically effective amount of a compound of claim 1.

5. The compound of claim 1 wherein
  X is carbonyl,
  $R_1$ is hydrogen, chlorine, or bromine in the 6- or 7-position,
  $R_2$ and $R_3$ and alkyl of 1 to 2 carbon atoms, and
  $n$ is 2 or 3.

6. The compound of claim 1 wherein
  X is methylene,
  $R_1$ is hydrogen,
  $R_2$ is methyl,
  $R_3$ is methyl, and
  $n$ is 2.

7. The compound of claim 1 wherein
  X is carbonyl,
  $R_1$ is hydrogen,
  $R_2$ is methyl, and
  $R_3$ is methyl, and
  $n$ is 3.

8. The compound of claim 1 wherein
  X is carbonyl,
  $R_1$ is 7-chloro,
  $R_2$ is methyl,
  $R_3$ is methyl, and
  $n$ is 2.

9. The compound of claim 1 wherein
  X is carbonyl,
  $R_1$ is 7-chloro,
  $R_2$ is methyl,
  $R_3$ is hydrogen, and
  $n$ is 3.

* * * * *